(12) United States Patent
Podda-Heubach

(10) Patent No.: US 8,517,233 B2
(45) Date of Patent: Aug. 27, 2013

(54) ASSISTANT SURGICAL DEVICE

(76) Inventor: Silvio Podda-Heubach, New York, NY (US)

( * ) Notice: Subject to any disclaimer, the term of this patent is extended or adjusted under 35 U.S.C. 154(b) by 62 days.

(21) Appl. No.: 12/672,377

(22) PCT Filed: Aug. 7, 2008

(86) PCT No.: PCT/EP2008/006529
§ 371 (c)(1),
(2), (4) Date: Jul. 27, 2010

(87) PCT Pub. No.: WO2009/019021
PCT Pub. Date: Feb. 12, 2009

(65) Prior Publication Data
US 2011/0163137 A1    Jul. 7, 2011

(30) Foreign Application Priority Data
Aug. 8, 2007  (DE) .................. 20 2007 011 044

(51) Int. Cl.
*A45F 5/00*    (2006.01)
(52) U.S. Cl.
USPC ............ 224/183; 224/197; 224/222; 224/267
(58) Field of Classification Search
USPC .................. 224/183, 197, 219, 221, 222, 267
See application file for complete search history.

(56) References Cited

U.S. PATENT DOCUMENTS

| 2,176,052 | A | | 10/1939 | Beyer | |
|---|---|---|---|---|---|
| 2,824,681 | A | | 2/1958 | Sorkin | |
| 3,942,194 | A | * | 3/1976 | Winter | 623/65 |
| 4,182,470 | A | * | 1/1980 | Atkinson | 224/183 |
| 5,201,444 | A | * | 4/1993 | Simonet | 224/183 |
| 5,333,767 | A | * | 8/1994 | Anderson | 224/183 |
| 5,353,974 | A | | 10/1994 | Maurizio | |
| D364,955 | S | * | 12/1995 | Gringer et al. | D3/228 |
| 6,530,508 | B1 | * | 3/2003 | Devine | 224/183 |
| 6,587,022 | B1 | * | 7/2003 | Devine | 335/285 |
| D493,957 | S | * | 8/2004 | Balliet | D3/228 |
| 6,945,503 | B2 | * | 9/2005 | Cohen | 248/206.5 |
| 2009/0050657 | A1 | * | 2/2009 | Woolery | 224/183 |
| 2010/0025442 | A1 | * | 2/2010 | Shurm | 224/183 |

FOREIGN PATENT DOCUMENTS

| GB | 30395 | 0/1911 |
|---|---|---|
| JP | 2003219904 A | 8/2003 |
| WO | 2004080236 A2 | 9/2004 |

* cited by examiner

*Primary Examiner* — Justin Larson
(74) *Attorney, Agent, or Firm* — Fish & Richardson P.C.

(57) ABSTRACT

A holder for surgical instruments that includes a device for holding the instruments, an arrangement for detachably fastening the holding device to the arm of a user and a coupling device for connecting the holding device and the fastening arrangement. The holding device includes a magnetic energy source.

16 Claims, 7 Drawing Sheets

ASSISTANT SURGICAL DEVICE

CROSS REFERENCE TO PRIOR APPLICATIONS

Figure 1:
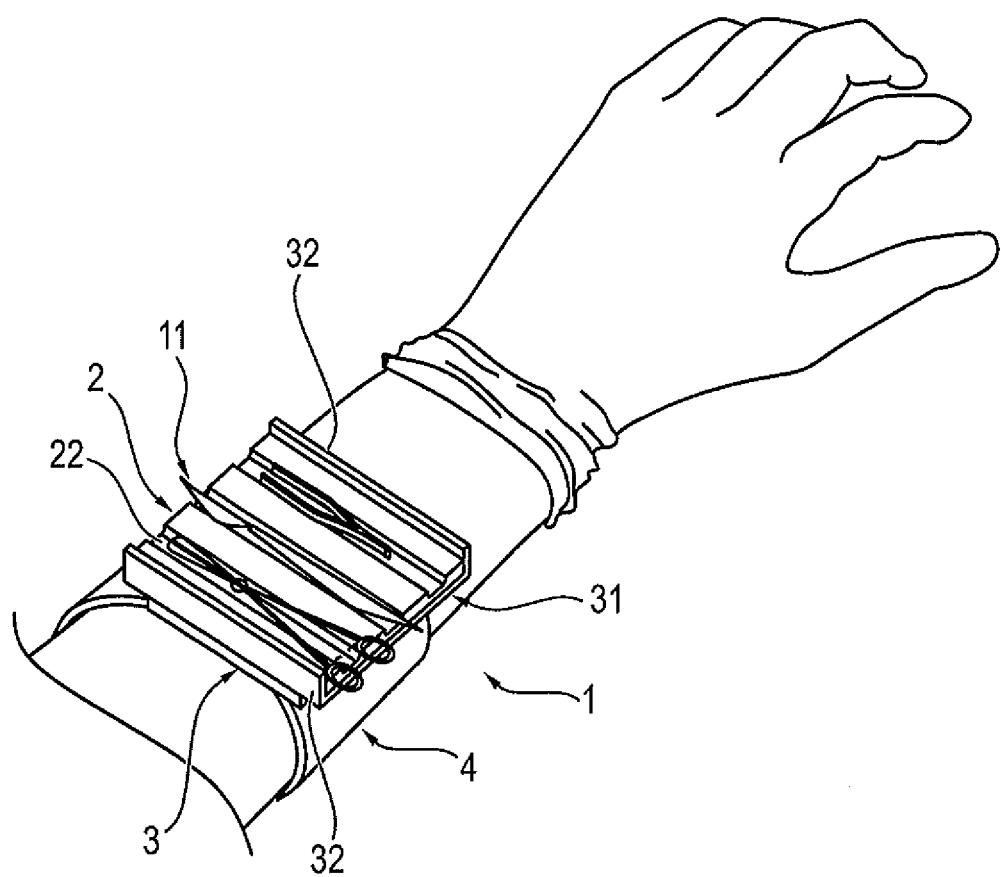

This is the U.S. National Phase application under 35 U.S.C. §371 of International Patent Application No. PCT/EP2008/006529, filed Aug. 7, 2008, and claims the priority of German Patent Application No. 20 2007 011 044.8, filed Aug. 8, 2007 both of which are incorporated by reference herein. The International Application published in German on Feb. 12, 2009 as WO 2009/019021 under PCT Article 21(2).

The present invention refers to a holder for providing surgical instruments for the direct access of an operator during an operation on a human or animal body.

A surgical procedure on a human or animal body requires the repeated performance of certain acts, gestures and movements. Specifically, a surgical procedure requires the continuous exchange of surgical instruments between the operator and an assisting person. This exchange gives rise to an unnecessary additional expenditure of time and in addition implies an increased risk of injury for all parties within certain phases of a procedure, during which several different instruments are required in quick exchange, in fact regardless of if the surgical procedure is carried out in a hospital, within the scope of an ambulant treatment, on the place of an accident, or in a medical practice. In any case, the continuous exchange of surgical instruments between the operator and the assistant personnel is unavoidable and bears possible risks and consequences under the conventional situations.

In addition, it is not infrequent that a required instrument cannot be found as quickly as required, falls down from the area of operation and gets contaminated or, even worse, gets lost during the operation. Longer delays during provision of surgical instruments are not unusual in clinical workday life and occur in particular, if assisting personnel changes multiply times during longer operations. In addition, an increased risk for the patient as well as the operator exists in particular, when scissors, forceps and needle holders usually are provided on a stationary stand ("Mayo stand") in the operation area or over a tablet directly on top of the patient during suturing long incisions.

It is therefore desirable to improve the ergonomic conditions during a surgical procedure in a way allowing the surgeon direct access to a certain number of instruments during an operation and reducing the additional expenditure of time because of continuous movement of surgical instruments in and out of the operational area as well as alleviating the risk of an injury for all parties.

Similar problems have been known from the prior art during carrying out certain daily handicraft actions requiring frequent exchange of tools for fulfilling certain tasks directly on site. For instance in the tailors trade, a direct access to pins is required during the fitting of a piece of clothing. As a rule, a so called pincushion is used for providing required pins in this case. This is a small, for example hemispherically shaped cushion, in which pins are stuck for removal and featuring a firm connection to a bracelet to be worn on the forearm by the user in use. Such pincushions enable a direct provision of the necessary pins in an ergonomic manner and permit an uninterrupted and time-saving work.

It is clear, however, that such a pincushion only is suitable for provision of very small and particularly lightweight tools which in addition must be able to be stuck in the pincushion. Any attempt to hold a weightier instrument on it must fail merely because of the elastic properties of the cushion material. In other words: Such use is excluded, even because of the very risk of injury to the applicant and/or risk of damage of the instrument when falling down.

It is therefore the object of the invention to directly provide also relatively large and weighty magnetic surgical instruments of most various shapes in an ergonomic and safe manner during the course of a surgical procedure and in this way contribute to saving of time in an operation as well as an extensive reduction of the risk of injury for all parties. This object is achieved in that, in a holder with a holding means for fixing the instruments, a fastening means for detachably fastening the holding means to the arm of a user and a coupling means for making a coupling between the fastening means and the holding means according to the preamble of claim 1, the holding means comprises at least one means for generating a magnetic field for temporarily fixing the instruments.

The inventive holder enables in an advantageous way the ergonomic provision of selected instruments in every phase of an operation. In particular, the inventive holder enables the operator at any time and directly access to the respective required instruments with the dominant hand during a surgical procedure without having to rely on assistance from assistant personnel and/or stationary carrying devices known in the art.

The inventive holder proves particularly advantageous in that it allows the operator total control of the immediately required instruments and insofar makes him independent of attention of assistant personnel.

A further advantage is that the inventive holder contributes to optimizing the operational conditions by allowing an ergonomic access to the relevant surgical instruments during a procedure. In other words: by using the inventive holder, the effort of motion and the required space of the operator during a procedure are reduced in an advantageous way, which in turn contributes to a reduction of operator fatigue and in addition reduces the risk of distraction of the operator, which in turn improves safety of all parties. As a result, the invention can improve productivity as well as quality of work of the operator as well.

It is a further advantage that by using the inventive holder the risk of contamination of the surgical instruments during a procedure can be markedly reduced, because the operator himself has direct access to the instruments. In parallel, the risk of injury to the assistant personnel, the operator and the patient are reduced.

In cases where both forearms of the operator need to be free, as e.g. for deep incisions, the holder can easily be moved up to the upper arm and additionally secured there, if necessary. Of course, it is likewise possible to remove the holder completely in such a case and keep it in a sterile environment until later use.

Because of its simple design, the holder can without any problems and quickly be adapted to the specific requirements of different cases of medical use and fields at any time, e.g. by correspondingly adapting the holding means or tablet, respectively, and/or using special adapters.

In addition, a particular advantage proves to be the small size and very limited weight of the holder on the forearm of the operator.

Finally, another advantage results from the fact that the inventive holder comprises only a few, robust, easily cleanable and sterilizable parts, which, in addition, are of simple design and can be produced cost-effectively by conventional methods of metal and plastics technology using materials commonly used in the field of medical equipment.

Advantageous embodiments of the invention result from the dependent claims and will further be explained as follows:

The inventive holder which also can be referred to as a personal assistant surgical device (PASD) comprises the holding means in form of a magnetic platform or tablet, respectively, for detachably placing the required surgical instruments thereon, which is detachably positioned on top of the non-dominant forearm of the operator. Shape, size and weight of the tablet depend on the type of operation to perform as well as size and number, respectively, of the instruments to hold and can therefore correspondingly be defined within wide limits. Preferably, the tablet is provided in rectangular, square, oval or round shape and enables placement of instruments in a substantially parallel arrangement.

According to a first embodiment the upper surface of the holding means is formed flat. Further embodiments of the holding means are provided with specific grooves, indentations and/or projections on the placement area in order to properly align and improve position stability of often required individual instruments such as—but not limited to—forceps, scissors, and blades. Preferably, the specific grooves, indentations and/or projections enable a parallel alignment of the instruments.

The means for generating a magnetic field are preferably arranged and dimensioned in a way that the field action extends substantially over the whole of the upper surface of the holding means or tablet, respectively, allowing to hold the placed instruments in any orientation. A field distribution over the whole surface is particularly suitable for holding relatively small instruments. Further embodiments of the holding means feature the magnetic force action in particular in the form of a dot matrix for holding instruments with a larger surface area or in stripes of substantially parallel alignment for holding instruments in perpendicular arrangement relative thereto on the upper surface as well as on the underside of the holding means.

The upper surface of the holding means is designed substantially parallel to the underside. According to a further embodiment the tablet features an upper surface being slanted relative to the underside, with angles of inclination between 0 and 30 degrees or, more particularly, between 5 and 15 degrees being preferred, for a particularly ergonomic access to the instruments during operation.

In order to ensure for the operator in each case an ergonomically optimal alignment of the holding means or tablet, respectively, on the forearm during the operation, this is pivotally or rotatably connected to a firm base. The table can be hold in an angular position relatively to the base via the named locking means. In this way, the holder is advantageously useable both on the left and on the right arm of an operator or suited for a right-handed as well as for a left-handed operator, respectively.

The relative positioning of the holding means to the fastening means and thus to the arm of the user is accomplished by the coupling means. For that, the coupling means comprises essentially two plane-parallel plates rotatably mounted around a common perpendicular central axis and held in their plane-parallel coordination by mechanical or magnetic means. In doing so, the relative rotation or angular coordination, respectively, between the two plane-parallel plates can be accomplished both continuously and in a step-by-step manner. Under usage condition of the holder one of the two plates—the bottom part of the coupling means—features a rotationally resistant connection to the fastening means while the other plate—the upper part of the coupling means—is connected to the holding means.

The magnetic connection between the upper part of the coupling means and the holding means, more particularly between the upper surface of the upper part and the underside of the holding means or tablet, respectively, is enabled in that the upper part at least partially is made of a magnetic material which is attracted by the magnetic field generating means of the holding part. The retention force depends on the size of the effective connecting area, the magnetic field intensity in the connecting area as well as the magnetic properties of the material used for the upper part and is thus clearly definable. The total mass to be hold, namely, the mass of the upper part, the holding means and the surgical instruments to hold is decisive for the design of the magnetically effective parameters. In order to ensure a defined angular relation between upper part and holding means under usage condition of the holder the upper part can be formed in the form of a receptacle having lateral walls restricting the holding means laterally. Preferably these lateral walls rise above the holding means, thus forming a mechanical barrier to avoid sliding of the instruments deposited on top of the upper surface.

Virtually any means known to a person skilled in the art can be used for rotationally resistant connection of the bottom part of the coupling means with the fastening means, more particularly, between the underside of the bottom part with the upper surface of the fastening means. For instance, the bottom part can be made rotationally resistant to the fastening means by bonding, screwing or a snap lock. Preferably however, two slots are provided in the underside of the bottom part into which a ribbon shaped fastening means is removably inserted. Further preferably two such fastening means being parallely spaced are provided in a corresponding way.

The rotatable connection of the bottom part with the upper part of the coupling means while maintaining a substantially plane-parallel coordination at a defined rotation angle is preferably realized mechanically by using a bayonet mount or a screw joint. A defined angular coordination between bottom and upper part is realized in case of the bayonet mount by correspondingly arranged gudgeon slot pairings. In case of the alternative use of a screw joint such angular coordination is achieved by counter means.

An alternative to the mechanical connection is the likewise preferred magnetic connection of the bottom part with the upper part. In this case the bottom part of the coupling means comprises a further means for producing a magnetic field which attracts the upper part made of at least partially magnetic material and connecting both parts in this way. For defining the common rotational axis of the bottom and the upper part the opposing plate areas comprise a protrusion and a corresponding indentation which both being in mating engagement under usage condition of the holder.

In accordance with the geometrical configuration of these mating surface areas per se any desired angular coordination between bottom part and upper part is possible. Thereby, the indentation can be provided in the bottom part and the protrusion in the upper part or vice versa. Preferably however, the indentation is provided in the bottom part and the protrusion in the upper part for inter alia making the upper part mechanically more stable in this way. For a continuously rotatable coordination of the upper and the bottom part the protrusion and the indentation are formed cylindrically; for a step-by-step relative rotation of the upper and the bottom part, forming of the connecting areas in the form of a meshing external and internal toothing is provided, with the positional change being done by detaching the upper part from the bottom part and reinserting in the newly desired angular position, i.e. changing over.

In this way, the number of possible angular positions of the holding means relative to the fastening means, or of the upper part of the coupling means relative to its bottom part, respectively, is arbitrarily selectable, since there are no restrictions as to the arrangement of the geometric pairing.

Moreover, it is also possible to provide for step-by-step positioning when the connecting areas are circularly made, by forming the facing surfaces with corresponding magnetic pairings, preferably in the circumferential region.

At least one bracelet is provided as a fastening means for detachably and securely fastening the holding means to the dorsal side of the non-dominant forearm of the operator, each preferably being formed as an endless elastic ribbon or as an open ribbon of an elastic or non-elastic material formed with a closure and comprising a sterilizable, preferably reusable material. Alternatively, at least a bracelet or at least an elastic ribbon made of a disposable material may be provided.

In the case of usage of only one fastening means, the rotationally resistant coordination with the coupling means is ensured by providing it with a wide area, for which purpose this, as already said, preferably contributes by two parallel guiding slots for receiving the ribbon shaped fastening means and thus reliably prevents a relative rotation between the coupling means and the fastening means thus preventing undesirable rotation of the holding means and the tablet, respectively, with the surgical instruments placed thereupon during an operation.

The same effect can be achieved by two fastening means being parallelly spaced and formed in the same way. In addition, the two fastening means provide a safety against unintended detachment during intended usage of the holder and opens the possibility to insert narrow ribbon, belt, or cord shaped fastening means, too.

Preferably, permanent magnets encased in plastic material are used as a means for generating the magnetic fields on the upper surface of the holding means as well as for magnetically connecting the bottom part and the upper part of the coupling means in accordance with the given alternative embodiment. Shape and field intensity of the magnets employed are determined in accordance with shape and weight of the parts to be hold, including the instruments, and in conventional way are dimensioned in a manner ensuring both a secure fixing and an easy detachment. Holding means or tablets, respectively, are provided with appropriately different magnetic field intensity and if necessary field distribution which are allocable by a proper coding, for instance by different coloration, for instruments of different weight. With regard to the maximum working temperature of the permanent magnets employed the requirements named below resulting from the particular use of the inventive holder are to be met.

All component parts of the inventive holder are made of sterile and/or sterilizable materials. Thus, the inventive holder comprises exclusively such components or materials which either already are provided in sterile form ready-to-use in a sterile environment, such as the alternatively used ribbons made of disposable materials or which are compatible with the sterilizing methods usually being used for medical instruments in laboratories and hospitals. Among these sterilizing methods are notably the steam sterilization and the plasma sterilization. Overall, as a consequence, all components and materials of the inventive holder have to meet the particular chemical and physical requirements including the enhanced requirements concerning temperature stability and disinfectant resistance.

Accordingly, the permanent magnets employed as a means for generating a magnetic field must have a maximum working temperature not below the maximum temperature occurring in the course of sterilization of the inventive holder. Maximum working temperature refers to the temperature a permanent magnet may be exposed to without losing its permanent magnetic properties. Generally, it is well below the Curie temperature of the corresponding permanent magnetic material.

Figure 2:
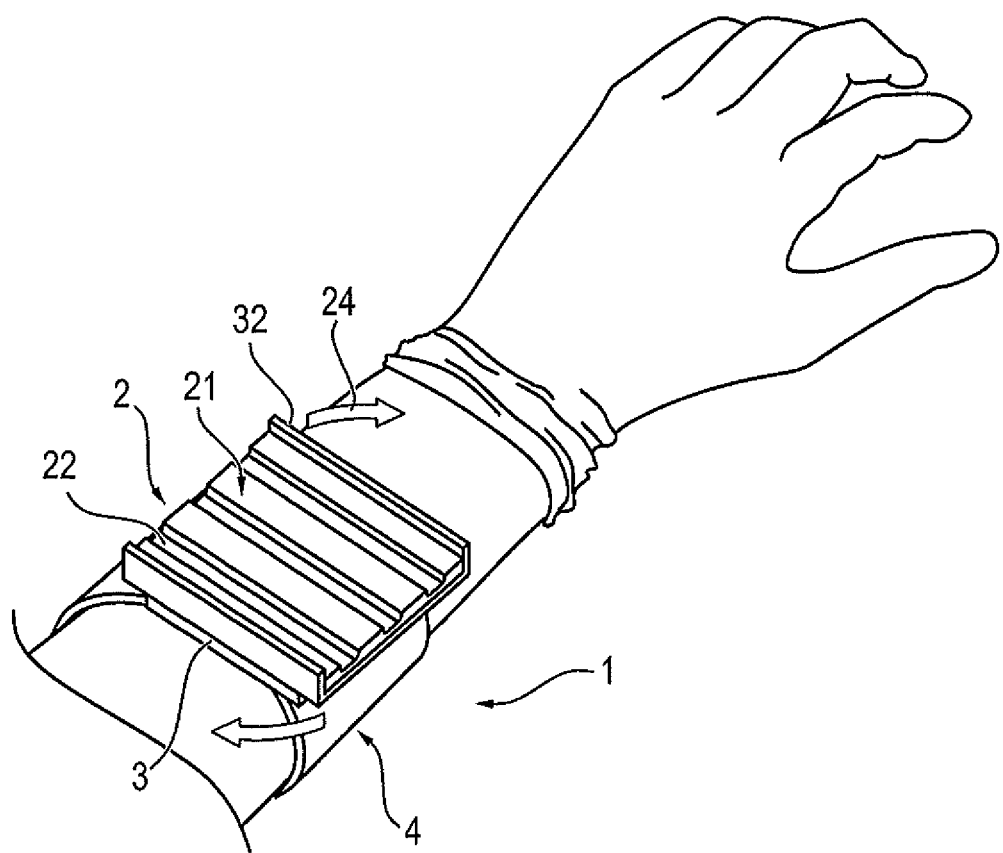
Figure 3:
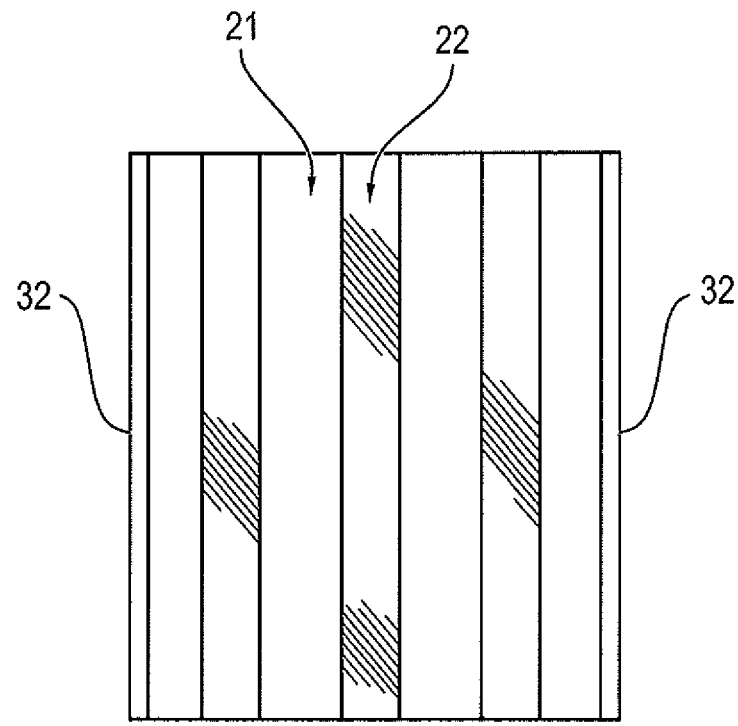
Figure 4:
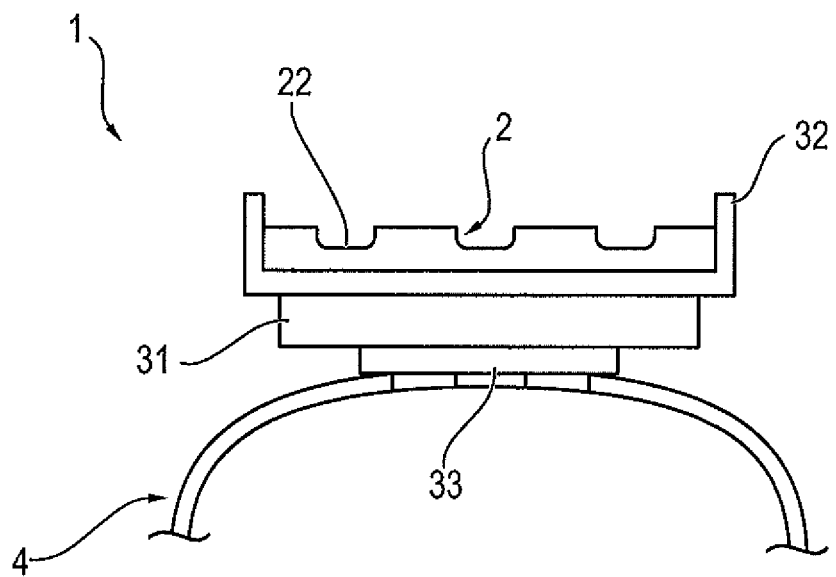
Figure 5:
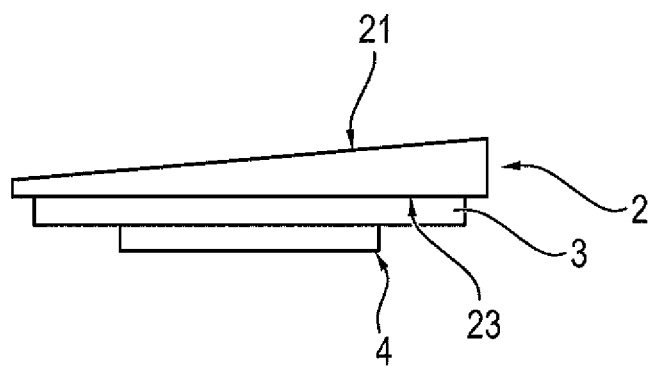
Figure 6:
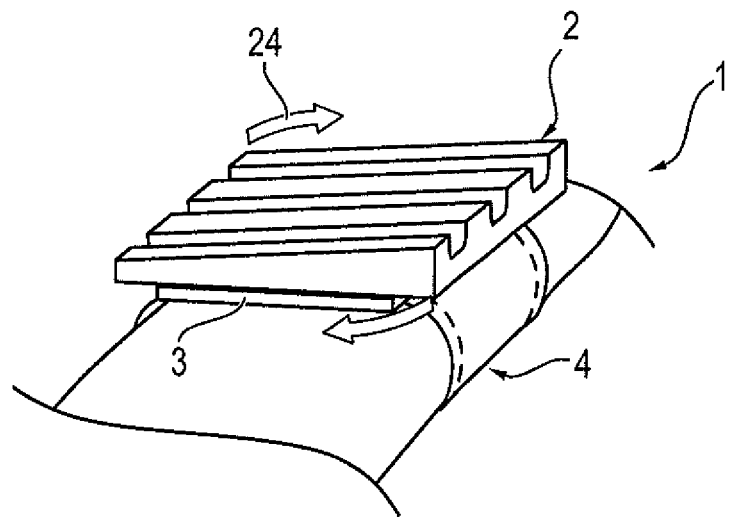
Figure 7:
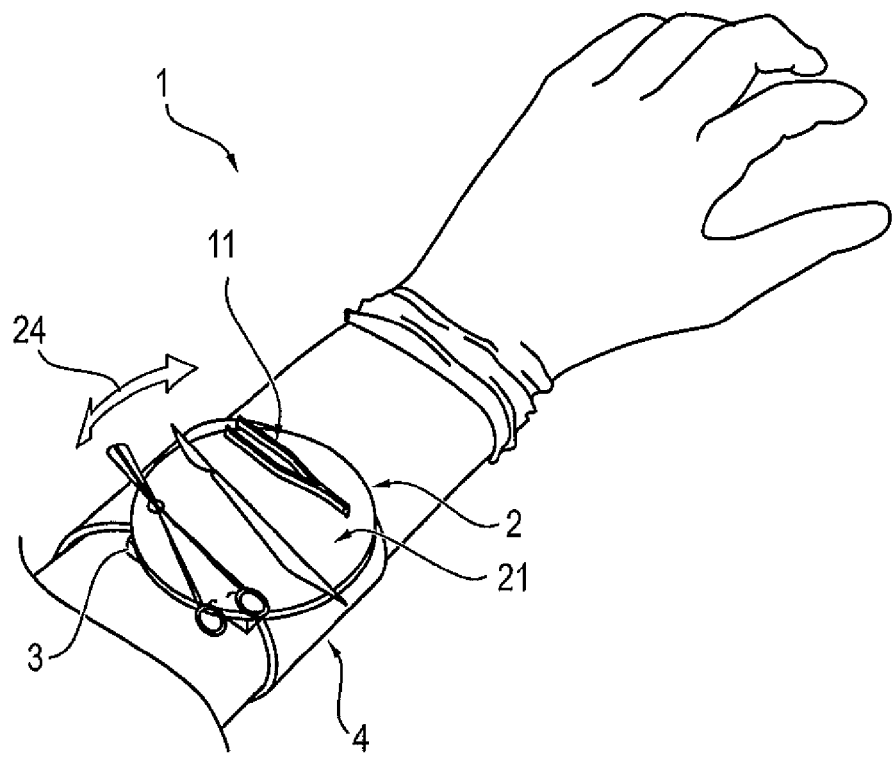
Figure 8:
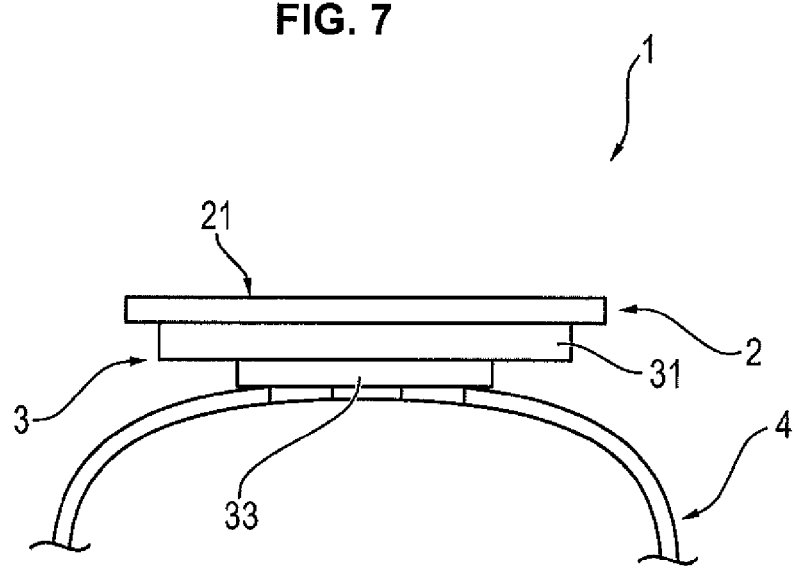
Figure 9:
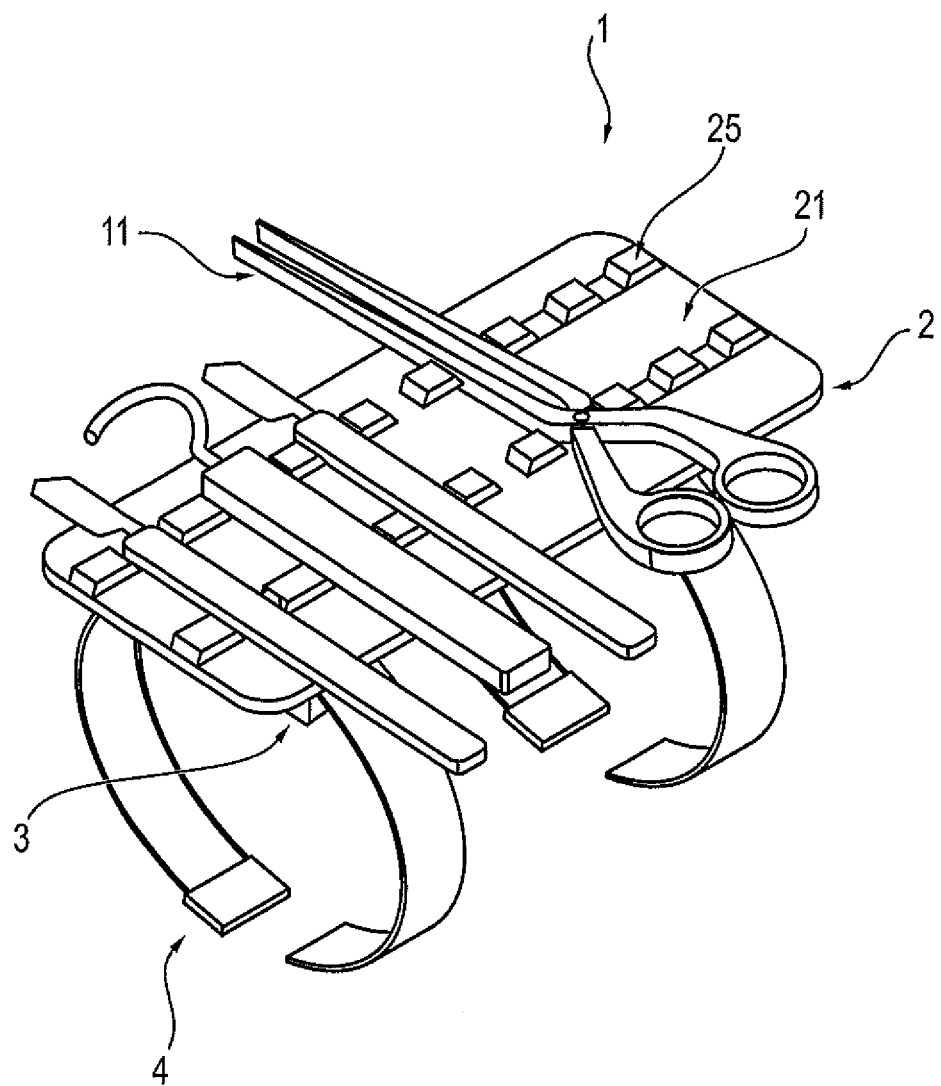
Figure 10:
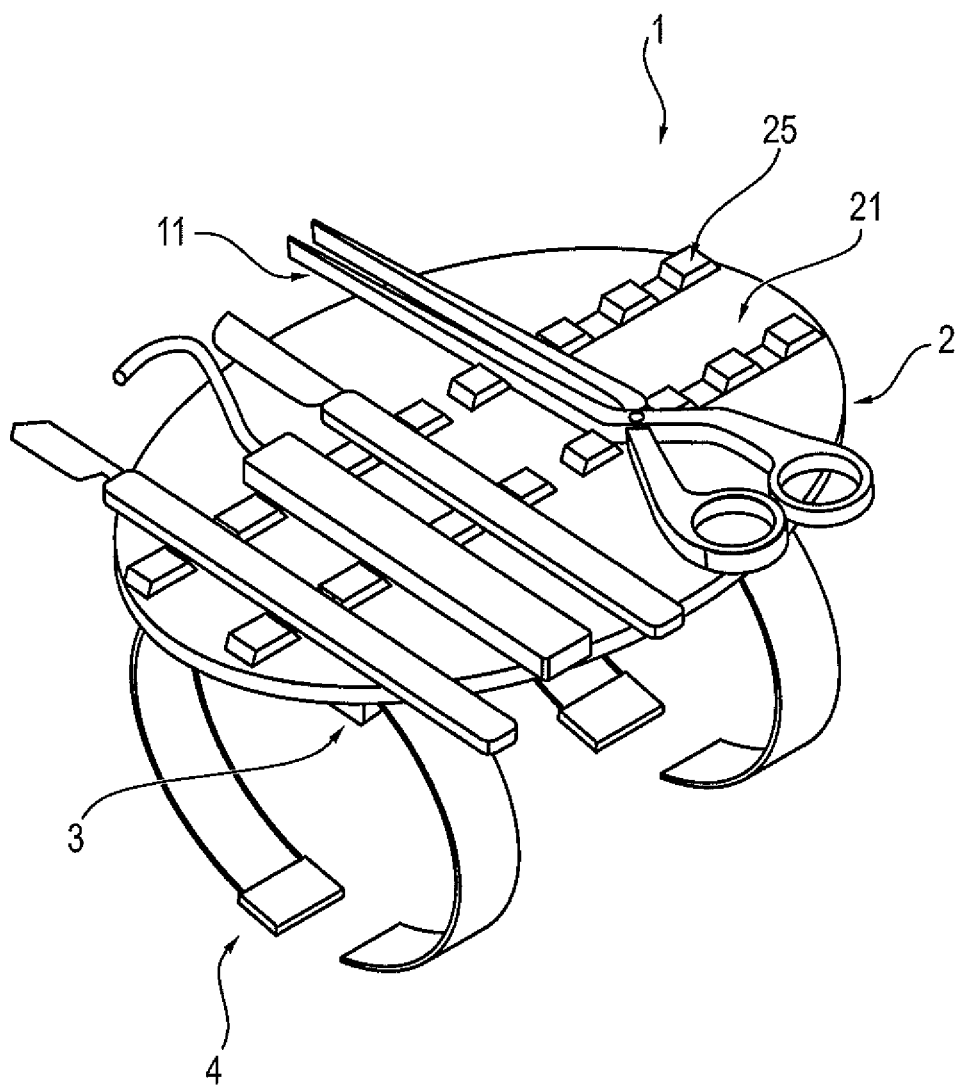

Details of the advantageous embodiments of the invention given in the dependent claims are also apparent from the drawings to be referred to respectively, with FIG. 1 showing a perspective view of an embodiment of the inventive holder in use with fastening means, a receptacle with lateral walls and a rectangular holding means guided therein with grooves in the upper surface and surgical instruments (forceps, blade, needle holder) hold therein, FIG. 2 showing the inventive holder of FIG. 1 without surgical instruments and with an indication of the direction of rotation of the holding means relative to the fastening means, FIG. 3 showing a top view of the inventive holder of FIG. 2, FIG. 4 showing a front view of the inventive holder of FIG. 2, FIG. 5 showing a side view of a further embodiment of the inventive holder with fastening means, coupling means and a holding means with an upper surface being slanted relative to the underside, FIG. 6 showing the inventive holder of FIG. 5 in perspective view in use with an indication of the direction of rotation of the holding means relative to the fastening means, FIG. 7 showing a further embodiment of the inventive holder in perspective view in use with a round holding means having a flat upper surface and surgical instruments (forceps, blade, needle holder) hold thereon with an indication of the direction of rotation of the holding means relative to the fastening means, FIG. 8 showing a front view of the inventive holder of FIG. 7, FIG. 9 showing a further embodiment of the inventive holder in a perspective view with a rectangular holding means having projections on the upper surface and surgical instruments (needle holder, blades, hook) aligned therewith, and with two fastening means, and FIG. 10 showing the inventive holder of FIG. 9 with an oval holding means instead of the rectangular holding means.

LIST OF REFERENCE NUMBERS 1 holder
11 surgical instruments
2 holding means
21 upper surface of the holding means
22 groove in the upper surface of the holding means
23 underside of the holding means
24 direction of rotation
25 projection on the upper surface of the holding means
3 coupling means
31 upper part of the coupling means/receptacle
32 lateral wall of receptacle
33 bottom part of the coupling means
4 fastening means

The invention claimed is:

1. A surgical instrument holder comprising a holding means for temporarily fixing the instruments in a fixed position, a fastening means for detachably fastening said holding means to the arm of a user, and a coupling means for making a connection between said fastening means and said holding means, wherein said holding means comprises at least one means for generating a magnetic field for temporarily fixing the instruments, said holding means being pivotally or rotatably connected to a firm base and said coupling means comprises two plates held substantially parallel and plane with one another and mounted around a common perpendicular central axis, said plates being retained in their plane-parallel coordination by magnetic means, wherein one of the plates forms a rotation resistant bottom part of the coupling means connected to the fastening means to form the firm plate, and the other plate forms an upper part of the coupling means and is connected to the holding means, the holding means being fixable in any angular position with respect to said base, wherein the upper surface of said holding means is that is an angle that is between about 0 and about 30 degrees to the lower surface of the holding means; wherein the upper part of the coupling means has a border that rises above the holding means and extends at least partially around the circumference of the holding means in order to prevent instruments from sliding off the holder.

2. A holder for surgical instruments comprising:
means for temporarily fixing the instruments in a first position,
means for detachably fastening and unfastening said temporary fixing means to the arm of a user, and
a coupling means for making a connection between said fastening means and said temporary fixing means, wherein said temporary fixing means comprises
at least one means for generating a magnetic field for temporarily fixing the instruments in the first position, said temporary fixing means being pivotally or rotatably connected to a firm base and said coupling means comprises two substantially planar-parallel plates mounted around a common perpendicular central axis, said plates being magnetically retained in their planar-parallel arrangement wherein a first one of the plates forms a bottom part of the coupling means, is resistant to rotation and connected to the fastening means to form the firm base, and the second plate forms an upper part of the coupling means and is connected to the temporary fixing means, the temporary fixing means being fixable in any angular position with respect to said base, and the upper part of the coupling means has a border that rises above the temporary fixing means and extends at least partially around the circumference of the holding means in order to prevent instruments sliding off the holder.

3. The holder according to claim 2, wherein said temporary fixing means has a substantially flat upper surface or one comprising grooves, indentations, and/or projections for temporarily fixing the instruments.

4. The holder according to claim 2, wherein the fastening means is at least one closed elastic ribbon or at least one open ribbon with a fastener for securely fastening on the arm of a user and in rotationally resistant cooperation with said coupling means.

5. The holder according to claim 2, wherein permanent magnets are provided as the means for generating a magnetic field.

6. The holder according to claim 2, wherein the upper part has the shape of a receptacle and has lateral walls that rise above the means for temporarily fixing.

7. The holder according to claim 2, wherein the temporary fixing means comprises sterile and/or sterilizable materials.

8. The holder according to claim 7, wherein the upper part being formed in the form of a substantially plane-parallel plate with magnetic properties for detachably connecting with said holding means.

9. The holder according to claim 2, wherein the magnetic field action is substantially effective over the whole temporary fixing means in the form of a dot matrix or in stripes of substantially parallel alignment on the upper surface and on the lower surface of said temporary fixing means, with at least one magnetic field generating means.

10. The holder according to claim 9, wherein the bottom part is detachably mounted on the fastening means.

11. The holder according to claim 10, wherein the upper part has the form of a plane plate that is substantially parallel to the lower plate and has magnetic properties for detachably connecting with said temporary fixing means.

12. The holder according to claim 11, wherein the upper part has the form of a receptacle with magnetic properties for detachably connecting with said temporary fixing means and with an at least in part circumferentially extending border for lateral restriction of said temporary fixing means in a working condition of the holder.

13. The holder according to claim 12, wherein the magnetic upper part is detachably connected with said temporary fixing means in a usage condition of the holder.

14. The holder according to claim 12, wherein the upper surface of said means for temporarily fixing is formed with an angle that is between about 0 and about 30 degrees to the lower surface of the means for temporarily fixing.

15. The holder according to claim 12, wherein the magnetic upper part has the form of a receptacle for detachably connecting with said temporary fixing means and with an at least in part circumferentially extending border for lateral restriction of said temporary fixing means in a usage condition of the holder.

16. The holder according to claim 15, wherein the bottom part is detachably mounted on the fastening means.

* * * * *